United States Patent [19]

Haugland et al.

[11] Patent Number: 4,945,171
[45] Date of Patent: Jul. 31, 1990

[54] XANTHENE DYES HAVING A FUSED (C) BENZO RING

[75] Inventors: Richard P. Haugland, Junction City; James Whitaker, Eugene, both of Oreg.

[73] Assignee: Molecular Probes, Inc., Eugene, Oreg.

[21] Appl. No.: 83,459

[22] Filed: Aug. 10, 1987

[51] Int. Cl.$^5$ ............................................. C07D 311/78
[52] U.S. Cl. ...................................... 549/224; 546/15; 549/297; 549/344
[58] Field of Search ....................... 549/224, 297, 344; 546/15

[56] References Cited

U.S. PATENT DOCUMENTS

| | | | |
|---|---|---|---|
| 3,896,116 | 7/1975 | Ozutsumi et al. | 546/15 |
| 3,996,212 | 12/1976 | Ozutsumi et al. | 549/224 |
| 4,503,148 | 3/1985 | Valet et al. | 549/223 |
| 4,510,251 | 4/1985 | Kirkemo et al. | 549/223 |
| 4,515,730 | 5/1985 | Valet et al. | 549/223 |
| 4,609,740 | 9/1986 | Rotman | 549/223 |
| 4,687,862 | 8/1987 | Obitsu et al. | 549/224 |

FOREIGN PATENT DOCUMENTS

| | | | |
|---|---|---|---|
| 0014725 | 6/1973 | Japan | 549/224 |
| 8065755 | 10/1981 | Japan | 549/224 |

OTHER PUBLICATIONS

O. Fischer & E. Konig, *Berichte* 47:1076, (1914).
O. Fischer & E. Konig, *Berichte* 50:1011, (1917).
N. N. Ghatak & S. Dutt, *J. Indian Chem. Soc.* 6:19, (1929).
M. L. Graber et al., *Analyt. Biochem.* 156:202, (1986).
A. M. Paradiso et al., *Nature* 325:447, (1987).
T. J. Rink et al., *J. Cell Biol.* 95:189, (1982).
J. A. Thomas et al., *Biochemistry* 18:2210, (1979).
G. Valet et al., *Naturwissenschaften* 68:265, (1981).
O. S. Wolfbeis et al., *Z. Anal. Chem.*, 314:119, (1983).

*Primary Examiner*—Asok Pal
*Attorney, Agent, or Firm*—Klarquist, Sparkman & Coe

[57] ABSTRACT

Synthesis and applications of fluorescent dyes which are derivatives of benzo[c]xanthenes is described. The dyes exhibit pH dependent absorption and fluorescence spectra with pKas near the normal physiological range. Unlike fluorescein, the dyes exhibit emission of different characteristic wavelengths dependent on the pH of the medium. This permits several methods of measuring the pH of the medium in contact with the indicator including measuring two emissions with one excitation, selectively exiting the acid and base forms independently and measuring their emission at either single or dual wavelengths, or measuring the characteristic pH dependent absorption or fluorescence excitation spectral. Methods are presented for making the indicators permeant to cell membranes for the measurement of intracellular pH.

25 Claims, 8 Drawing Sheets

XANTHENE DYES HAVING A FUSED (C) BENZO RING

BACKGROUND OF THE INVENTION

Acidity as measured by pH affects the rate and extent of chemical reactions. Measurement of pH of biological fluids is important for following the health of an organism. Furthermore, its measurement in individual cells and tissues has been correlated with response to external stimuli including drugs, ions, light and other cells. Acidity is also important in many non-biological systems and a variety of electrical and spectroscopic techniques have been developed for its measurement. Measurement of pH by optical sensors is an established technique. Absorption indicator dyes such as phenolphthalein have been used for visual or instrumental estimation of acidity for many years. The basic requirement for measurement with an optical indicator is a change in an optical property of the dye such as absorption or fluorescence that can be correlated with the pH of the medium. For the greatest sensitivity to small changes in pH of the medium, the equilibrium constant between the acidic and basic forms of the indicator for the dye (i.e. the $pK_a$) should be near the pH of the medium. For measurements in physiological media including blood and the interior of most cells, this is usually in the range of pH 6 to pH 8, commonly pH 7.0 to 7.6. An advantage of measurement of pH by a fluorescence technique rather than absorbance is the greater sensitivity of the measurement due to the intrinsically higher detectability of emitted light versus absorbed light. The correspondingly lower levels of sensor required permit measurements of the intracellular pH in single cells by such techniques as flow cytometry with concentrations of the sensor that have low toxicity and avoid buffering of the equilibrium.

Among the fluorescent dyes that have been used to estimate pH, the most common are β-methylumbelliferone, its derivatives, 8-hydroxypyrene-1,3,6-trisulfonic acid (pyranine)(Wolfbeis, et al., Z. Anal. Chem. 314, 119 (1983)), and fluorescein or its derivatives, carboxyfluorescein (Thomas, et al., Biochemistry 18, 314, 119 (1979)), and 2′,7′-bis-(carboxyethyl)-5(and-6)carboxyfluorescein (BCECF) (Rink et al., J. Cell. Biol. 95, 189 (1982)). Of these, only the fluorescein dyes have the long wavelength spectral properties comparable to the dyes in this invention. This includes absorbance at the primary wavelengths of the argon laser (488 and 514 nm). This laser is widely used in flow cytometry and fiber optic monitoring. Fluoresceins have pH dependent absorption and excitation spectrum and a $pK_a$ of approximately 6.4 to 7.0 depending on substituents. Measurement of pH dependent emission intensity changes in single cells with a single excitation wavelength gives spurious results since the intensity will be effected by dye concentration in the cell, by leakage of the dye out of the cell, cell thickness, and photobleaching of the dye. Measurement of pH by the emission intensity with a single excitation wavelength by use of a dye immobilized on a fiber optic suffers similar problems related to dye concentration, bleaching and path length. A more practical approach that reduces the effect of changes in dye concentration in the light path is to ratio the amount of fluorescence at a fixed wavelength with excitation at a pH sensitive wavelength to the amount of fluorescence at the same wavelength with excitation at a relatively pH insensitive wavelength. This is the technique commonly used to estimate the pH inside cells with fluorescein derivatives such as BCECF (Paradiso, et al., Nature 325, 477 (1987)). While this is quite practical for suspensions of cells and in homogeneous fluids in a fluorometer or a microscope, because measurement of pH by ratioing excitations requires excitation sources of two different wavelengths, this is usually impractical in flow systems including flow cytometers and fiber optic systems for continuous monitoring of the pH of flowing fluids, such as blood.

For the reasons outlined above, it is preferable in a flowing system to be able to excite the sensing dye at a single wavelength and to be able to monitor fluorescence emission at two wavelengths with the maximum emission in acidic solution at a different wavelength than in basic solution. Furthermore, it is strongly advantageous if the dye possesses excitation and emission wavelengths above 480 NM both to take advantage of current laser excitation sources and, in the case of biological fluids, to decrease the background from natural fluorescence in cells and fluids and to reduce the intrinsic light scattering artifacts (which decrease with the inverse fourth power of the wavelength). Only the dyes described in this invention have been reported to possess this and other desirable properties. In the pH range 5 to 9, emission from fluorescein and related derivatives is all from the base form with wavelengths that are essentially independent of the pH of the medium. This has been explained as being due to the higher acidity of the excited state relative to the ground state leading to emission from a single state. While the population of the excited state may be altered by a quenching of the *absorbance* by a change in pH of the medium, the *fluorescence* emission spectra for fluorescein-based dyes over the pH range 5 to 10 changes only in intensity and not in wavelength thus precluding ratioing of emission wavelengths (Graber, et al., Analyt. Biochem. 156, 202 (1986)).

Dihydroxyphthalonitrile (U.S. Pat. No. 4,503,148) shows pH dependent emission but suffers from a complex response to pH indicative of multiple equilibria and, since it has only relatively weak ultraviolet and near UV absorbance, cannot be excited with the principal wavelengths of the argon laser (488 nm and 514 nm) in common use in flow cytometry. Unlike the benzo[c]xanthene dyes that are the subject of this invention, the pH of the medium as indicated by this dye is not readily determinable by ratioing emission intensities. Furthermore, it cannot be directly immobilized on materials such as optical fibers without modification of its fluorescence properties and, due to its high membrane permeability, is not well retained by cells.

SUMMARY OF THE INVENTION

Compounds of the hereinafter described type of benzo[c]xanthene dyes exhibit a pH dependent equilibrium between protonated and deprotonated forms. The two forms exhibit *both* pH dependent absorption and pH dependent fluorescence spectra. The light absorption or fluorescence spectra at equilibrium may be correlated with the pH of the medium. The unusual long wavelength dual fluorescence emission and dual absorption properties of the benzo[c]xanthenes permits four methods of application:

METHOD 1

One excitation wavelength two emission wavelengths. The naphthol and naphtholate forms of the benzo[c]xanthene dyes may be excited simultaneously with a single wavelength and the fluorescence emissions quantified independently with the ratio of the fluorescence emission intensities correlated with the pH of the medium.

METHOD 2

Two excitation wavelengths and two emission wavelengths. The naphthol and naphtholate forms of the benzo[c]xanthene indicator dyes may be excited independently and emission of the two forms measured independently with the ratio of the fluorescence emission intensities correlated with the pH of the medium.

METHOD 3

One emission wavelength and two excitation wavelengths. The excitation spectra with respect to fluorescence emission of the benzo[c]xanthene indicator dyes may be measured at a suitable emission wavelength and correlated with the pH of the medium. Alternatively, the emission intensity can be monitored at two discrete excitation wavelengths and the ratio of the intensities of fluorescence with excitation at the two wavelengths correlated to the pH of the medium.

METHOD 4

The ratio of absorption at two wavelengths or the entire absorption spectrum for the benzo[c]xanthene indicator dyes can be correlated with the pH of the medium.

OBJECTIVES

It is an object of this invention to provide a class of novel compounds.

It is also an object of this invention to provide fluorescent benzo[c]xanthene dyes.

It is also an object of this invention to provide novel long wavelength dual emission and dual absorption pH indicators.

It is also an object of this invention to provide fluorescent pH indicators in which the protonated and deprotonated forms of the indicator can be excited at one wavelength and emit at different wavelengths.

It is also an object of this invention to provide fluorescent pH indicators in which the protonated and deprotonated forms may be excited independently and their emissions quantified independently.

It is also an object of this invention to provide fluorescent pH indicators in which emission may be observed at a fixed wavelength and the excitation of the protonated and deprotonated species may be determined quantitatively at variable wavelengths.

It is also an object of this invention to provide materials and methods for making these dyes permeant to biological cells.

It is also an object of this invention to provide fluorescent extended conjugation analogs of fluorescein, carboxyfluorescein, biscarboxyethyl carboxyfluorescein (BCECF) and the like, compounds which have been found to have wide utility as pH indicators, fluorescent tracers and laser dyes.

It is also an object of this invention to provide fluorescent compounds which have many of the properties of fluorescein but absorb and emit light at longer wavelengths than fluorescein.

It is also an object of this invention to provide fluorescent benzo[c]xanthene dyes with amino and alkylamino substituents that possess hybrid structures between fluorescein and rhodamine and have pH sensitive spectral properties.

DETAILED DESCRIPTION OF THE PREFERRED EMBODIMENTS

Figure 1A:
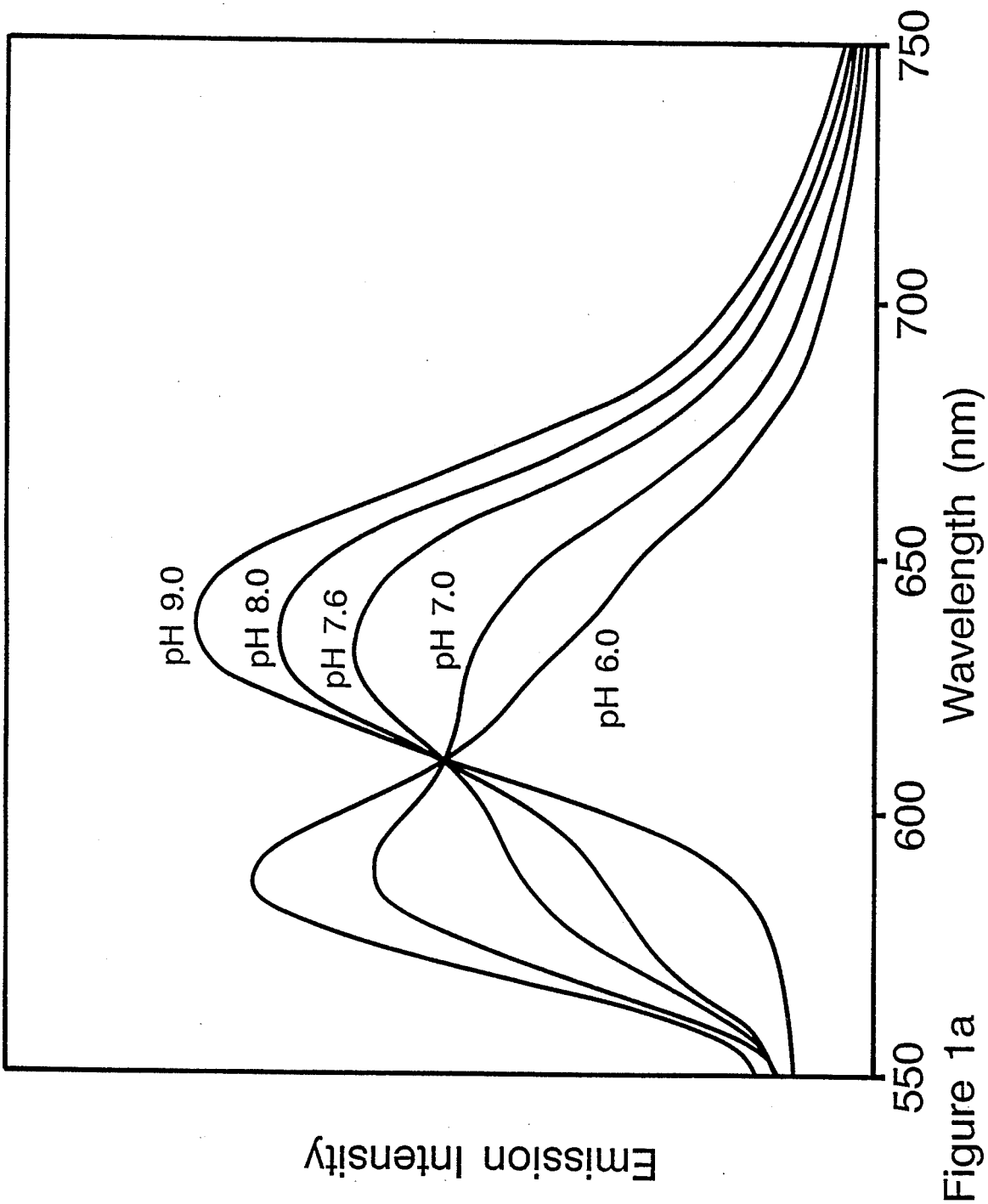
FIGS. 1a and 1b: observation of dual emission with a single excitation is shown in FIG. 1 for compound 8. Solutions of the dye in buffers of defined pH were excited at 514 and emission recorded (FIG. 1a). The ratio of the emission intensity at 636 nm versus 610 nm and of emission at 587 nm versus 610 nm were determined as a function of pH (FIG. 1b).

These and other objects and advantages are accomplished by providing a class of xanthene dyes having joined at the [c] face, a rigid, aromatic ring system having the formula:

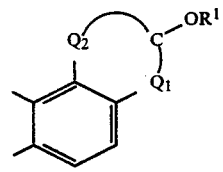

Wherein $Q_1$ and $Q_2$ of structure 1 represent the atoms necessary to form an unsaturated chain of 4 carbon atoms and which complete a fused, 6 member aromatic ring characterized by unsaturation of all atoms of the ring such that $Q_2$ contains 2 carbon atoms and $Q_1$ contains one carbon atom and $R^1$ is a member of the group consisting of a hydrogen atom, an alkali metal, ammonium, mono-, di-, tri-, or tetraalkyl ammonium ion, an alkyl group having 1 to 10 carbon atoms including substituted alkyls, a formyl, acetyl, or aliphatic acid ester having 1 to 18 carbon atoms including substituted aliphatic acids, benzoyl or aromatic acid ester or substituted aromatic or heterocyclic acid ester containing 4 to 20 carbon atoms.

More specifically, the preferred compounds of this invention conform to the formula:

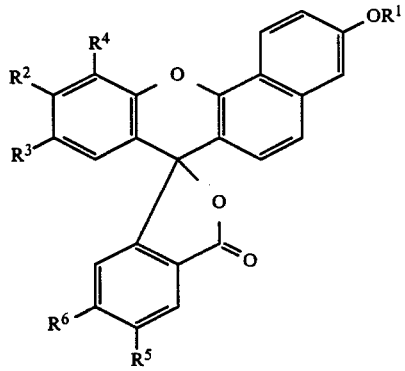

Wherein $R^1$ is as defined for the structure I and $R^2$ of structure II is a member of the group consisting of oxygen, substituted oxygen, nitrogen or substituted nitrogen. Specific embodiments include benzo[c]xanthene dyes wherein $R^2$ is from the group hydroxy, an alkali metal, ammonium, mono-, di-, tri-, or tetraalkyl ammonium salt of hydroxy, an alkoxy or arylalkoxy group having 1 to 18 carbon atoms, a formate, acetate or fatty acid ester having 1 to 18 carbon atoms, including substituted aliphatic acid esters, a benzoate or aromatic carboxylic acid ester having 4 to 20 carbon atoms including substituted and heterocyclic aromatic acids, an amine or ammonium, an alkyl amine or dialkylamine containing 1 to 12 carbon atoms, an alkyl or dialkyl amine containing 3 to 18 carbon atoms which, in conjunction with $R^3$ and/or $R^4$, is chemically bonded to the aromatic ring of the benzo[c]xanthene and which completes one or two 5 to 7 membered heterocyclic rings, an aliphatic or aromatic amide containing 1 to 18 carbon atoms including substituted amides such as amino acid amides, a cyclic amine containing to 4 to 8 carbon atoms such as pyrrolidine, morpholine and other cyclic amines, a cyclic lactam or cyclic imide containing 4 to 10 carbon atoms; $R^3$ and $R^4$ may be, in any combination, a hydrogen atom, a halogen atom, an alkyl or substituted alkyl containing from 1 to 20 carbon atoms, a carboxylic acid or aliphatic acid containing 2 to 20 carbon atoms and alkyl esters thereof, such as 2-(methoxycarbonyl)ethyl; $R^5$ and $R^6$ are members of the group consisting of a hydrogen atom, alkyl or substituted alkyl, amino or substituted amino, carboxylic acid, carboxamide or substituted carboxamide, carboxylic acid ester or sulfonic acid, and $R^5$ may or may not be identical to $R^6$.

It is to be understood that the 3,10bis-hydroxy compounds and the 3-hydroxy, 10-amino (or substituted amino) compounds can tautomerize between structures such as those represented below:

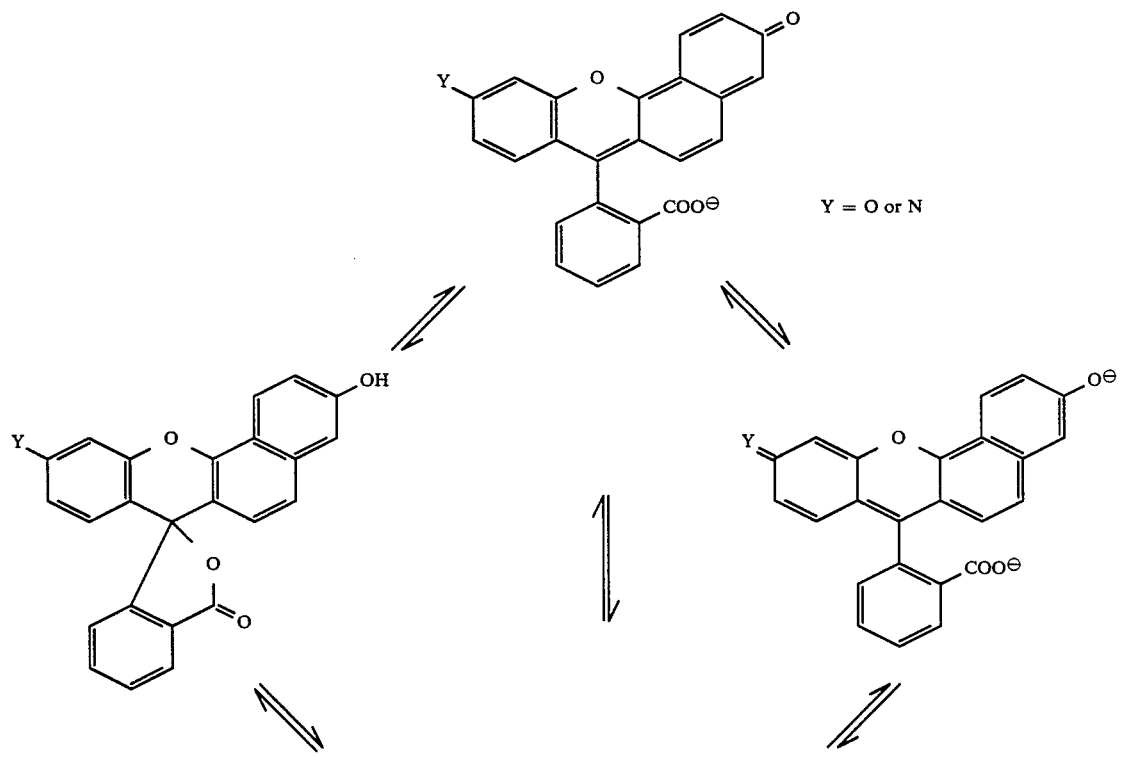

-continued

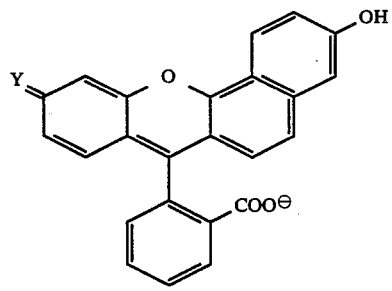

The predominance of each of the tautomeric forms as well as the mono and dianionic forms (3 and 4) is dependent upon choice of solvent and upon the pH of the solution.

In the case of the bis- and mono-hydroxy benzo[c]x-anthenes in aqueous solution above pH 5, the following pH dependent equilibrium is established:

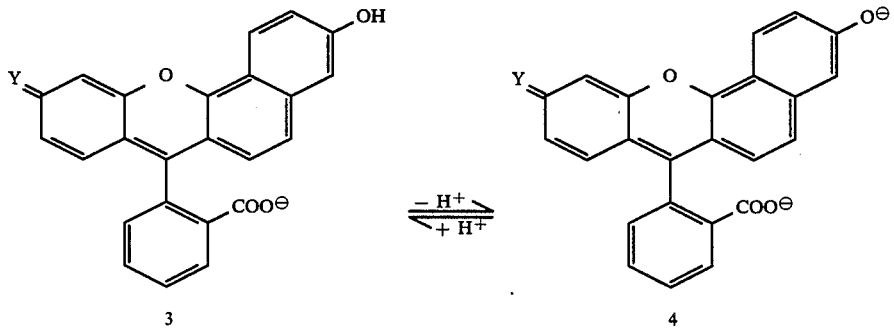

Unlike fluorescein-based dyes, both the naphthol form (3) and the naphtholate form (4) are intrinsically fluorescent with the absorption and emission maxima typically occurring at longer wavelengths for the basic form (4) than for the acidic form (3). The relative concentrations of the two forms are determined by the acidity or basicity of the solution in which they are present as well as by substituents of the specific compounds as defined in structure 2.

EXPERIMENTAL

The following details of synthetic procedures are intended to provide a method for someone skilled in the art to prepare selected examples of the desired compounds in this patent. The examples are not intended to limit or to exhaust the possibilities for synthesis of related materials that are considered as falling within the scope of this invention.

In general, the novel synthetic step of the procedure that results in formation of the new benzo[c]xanthene fluorophores that are the subject of this invention is condensation of 1,6-dihydroxynaphthalene with a substituted or unsubstituted 4-acylresorcinol or 6-acyl-3-aminophenol (or substituted amino) in the presence of a Lewis acid catalyst such as zinc chloride or a dehydrating acid such as polyphosphoric or sulfuric acid. Alternatively, the same products can be prepared by condensing a substituted or unsubstituted resorcinol or amino phenol with a substituted or unsubstituted 2-(acyl)-1,6-dihydroxynaphthalene in the presence of a Lewis acid catalyst. Subsequent modifications of the dyes before or after purification give the esters, ethers and amides that are also considered part of this invention. Table 1 gives a tabulation of several novel benzo[c]xanthene derivatives that have been prepared.

TABLE 1

| COMPOUND | $R^1$ | $R^2$ | $R^3$ | $R^4$ | $R^5$ | $R^6$ |
|---|---|---|---|---|---|---|
| 1 | H | OH | OH | H | H | H |
| 2a* | H | OH | H | H | H | COOH |
| 2b* | H | OH | H | H | COOH | H |
| 3 | H | OH | Cl | H | H | COOH |
| 4a | H | OH | $CH_2CH_2COOH$ | H | H | COOH |
| 4b | H | OH | $CH_2CH_2COOH$ | H | COOH | H |
| 5 | H | $Me_2N$ | H | H | H | H |
| 6 | H | $Et_2N$ | H | H | H | H |
| 7 | H | EtNH | Me | H | H | H |
| 8 | H | $Me_2N$ | H | H | H | COOH |
| 9 | H | $Et_2N$ | H | H | H | COOH |
| 10a | H | EtNH | Me | H | H | COOH |
| 10b | H | EtNH | Me | H | COOH | H |
| 11 | H | J** | J** | J** | COOH | H |
| 12a | H | OMe | H | H | H | COOH |
| 12b | H | OMe | H | H | COOH | H |
| 13a | Me | OH | H | H | H | COOH |
| 13b | Me | OH | H | H | COOH | H |

STRUCTURES OF BENZO[C]XANTHENE INDICATORS

TABLE 1-continued

STRUCTURES OF BENZO[C]XANTHENE INDICATORS

| COMPOUND | R¹ | R² | R³ | R⁴ | R⁵ | R⁶ |
|---|---|---|---|---|---|---|
| 14 | C(=O)Me | NMe₂ | H | H | COOH | H |
| 15 | C(=O)Me | NMe₂ | H | H | C(=O)OCH₂OC(=O)Me | H |
| 16 | C(=O)Me | OC(=O)Me | H | H | H | H |
| 17a | C(=O)Me | OC(=O)Me | H | H | H | COOH |
| 17b | C(=O)Me | OC(=O)Me | H | H | COOH | H |
| 18 | C(=O)Me | OC(=O)Me | Cl | H | H | COOH |

NOTES TO TABLE 1
Me = CH₃, Et = CH₂CH₃, C(=O) = a carbonyl group
*a or b after the number of a compound refers to components of an isomeric mixture
**J refers to part of the fused julolidino ring in the following ring structure:

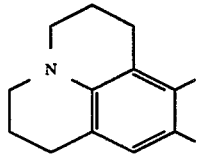

Condensation of 1,6-dihydroxynaphthalene with phthalic anhydride to yield a symmetric dibenz[c,h]xanthene termed "naphthofluorescein" has been previously reported (Fischer and König, Berichte 47 1076 (1914)) however this dye does not conform to the structure of the dyes in this invention. A limited number of fused benzo[c]xanthenes have been described that do not conform to the general structure of the dyes in this invention. To develop appreciable fluorescence and pH sensitivity, the extended conjugation of the 3,10-dihydroxy and 3-hydroxy-10-amino derivatives and their tautomers is required and these have not been previously been reported.

4-Acylresorcinols of utility for preparing benzo[c]xanthenes are conveniently prepared by treatment of fluorescein or substituted fluoresceins including but not limited to 4',5'-dimethylfluorescein, 2',7'-dichlorofluorescein, 2',7'-bis(carboxyethyl)-5(and-6)carboxyfluorescein (BCECF), 5-(and-6)carboxyfluorescein (mixed or separated isomers) and 5-(or-6)aminofluorescein with strong base at an elevated temperature (Ghatak and Dutt, J. Indian Chem. Soc. 6, 19 (1929)) or by condensation of resorcinol or a substituted resorcinol with phthalic anhydride or a substituted phthalic anhydride under approximately equimolar conditions.

6-Acyl-3-aminophenols (or substituted amino) can be prepared by an analogous hydrolysis of a symmetrical rhodamine dye including but not limited to rhodamine B, rhodamine 6G, carboxytetraalkylrhodamine, rhodamine 101, or 5-(or-6)-aminotetraalkylrhodamine or such, with strong base at an elevated temperature. Alternatively, 6-acyl-3-dialkylaminophenols can be prepared by acylation of a dialkylaminophenol with one equivalent of an anhydride (Ger. Offen. 3,018,546).

2-(Acyl)-1,6-dihydroxynaphthalenes can be prepared by base hydrolysis of the dibenz[c,h]xanthenes such as naphthofluorescein (and its substituted derivatives) or by condensation of 1,6-dihydroxynaphthalene with a substituted or unsubstituted phthalic anhydride derivative (Fischer and König, Berichte 50, 1011 (1917)).

Esters of the benzo[c]xanthenes provide a convenient method of making the dyes permeant to cell membranes (Valet, et al., Naturwissenschaften 68, 265 (1981); Thomas, et al., (1979); Rink, et al., (1982)). Inside the cells, non-specific esterases hydrolyze the esters, resulting in liberation of the pH indicator. The acetates and the acetoxymethyl esters have been the most commonly used permeant forms for loading cells.

EXAMPLE 1

Preparation of 3,10-dihydroxy-spiro[7H-benzo[c]xanthen-7,1'(3'H)-isobenzofuran]-3'-one, 1 and its diacetate 16.

A mixture of 6.0 g 2-(2',4'-dihydroxybenzoyl)benzoic acid, 4.2 g 1,6-dihydroxynaphthalene, and 6.1 g anhydrous zinc chloride was heated at 160° to 165° C. for 1 hour. The cooled melt was pulverized and washed several times with boiling water and air dried. The crude dye was refluxed in 50 ml acetic anhydride for 1½ hours and concentrated to about 25 ml by boiling. The residue was poured into water and stirred at about 50° for 30 minutes. The warm water was decanted and the residue was stirred in water at room temperature for 1 hour. The solid was collected by filtration and air dried. The crude diacetate was recrystallized once from toluene/isopropyl alcohol then once from chloroform/isopropyl alcohol to give 6.1 g slightly orange tinged crystals of 16 (MP=124°-126° C.).

A portion of the diacetate, 16, (2.5 g) was dissolved in 20 ml of 2M potassium hydroxide in methanol and 10 ml water was added. The mixture was stirred at about 50° C. for 2 hours. After addition of 40 ml water the methanol was removed by distillation. Acidification with glacial acetic acid, filtration and drying gave 1.86 g of compound 1 as an orange powder. R$_f$=0.36 with methanol:chloroform (1:9).

EXAMPLE 2

Preparation of [h,i]julolidino-spiro[7H-benzo[c]xanthen-7,1'(3'H)-isobenzofuran]-3'-one, 11.

The precursor, 7-(2',4'-dicarboxybenzoyl)-8-hydroxyjulolidine, was prepared by the condensation of benzene-1,2,4-tricarboxylic anhydride with 8-hydroxyjulolidine followed by separation of the isomers by fractional crystallization. A solution of 2.9 g of the acyl julolidine in 40 ml concentrated sulfuric acid was stirred at room temperature as 2.4 g 1,6-dihydroxynaphthalene was added in small portions over 30 minutes. After stirring an additional one hour, the mixture was poured over 600 ml ice water. The solid was collected and dried. The crude dye was converted to its dimethyl ester for purification by refluxing 3 days in 200 ml methanol containing 0.7 g p-toluene sulfonic acid. The mixture was evaporated, dissolved in chloroform, then washed with aqueous sodium bicarbonate and water. After drying and evaporation, the crude dimethyl ester was chromatographed over silica gel, first with a gradient of 3 to 12% methanol in chloroform and then with a gradient of 3 to 10% methanol in chloroform containing 1% triethylamine. The combined, evaporated fractions were hydrolyzed with potassium hydroxide in aqueous methanol, acidified, and the solid was collected to give, after drying, 0.5 g blue violet powder of compound 11, $R_f = 0.20$ with methanol:chloroform:acetic acid (15:82:3).

EXAMPLE 3

Preparation of 5'-(and-6')carboxy-3-hydroxy-10-methoxy-spiro[7H-benzo[c]xanthene-7,1'(3'H)-isobenzofuran]-3'-one, 12.

In a flask were combined 100 mg 2-[2',4'(and-5')-dicarboxybenzoyl]-1,6-dihydroxynaphthalene (prepared by basic hydrolysis of 5-(and-6)-carboxynaphthofluorescein), 50 mg 3-methoxyphenol and 130 mg zinc chloride. After heating at 155°–165° C. for 30 minutes, the cooled melt was pulverized and washed well with water. The crude dye was purified by chromatography over silica gel, first with 10% methanol in chloroform, then with 5% methanol in chloroform to give 76 mg reddish-brown solid, $R_f = 0.29$ with methanol:chloroform (1:4). Absorbance maximum in 40 mM potassium phosphate buffer at pH 9.0 at 542 nm, extinction coefficient of 21,100 $cm^{-1} M^{-1}$.

EXAMPLE 4

Preparation of 5'-(and-6')carboxy-10-hydroxy-3-methoxy-spiro[7H-benzo[c]xanthene-7,1'(3'H)-isobenzofuran]-3'-one, 13.

To a solution of 100 mg 5'-(and-6')-carboxy-3,10-dihydroxy-spiro[7H-benzo[c]xanthene-7,1'(3'H)-isobenzofuran]-3'-one (compound 2) in 5 ml 5% aqueous potassium hydroxide was added 1 ml dimethyl sulfate followed by dropwise addition with stirring over 2 hours of 15 ml 5% aqueous potassium hydroxide. Methanol, 10 ml, was added and the mixture heated one hour at 50° C. The mixture was poured into water, acidified with hydrochloric acid and extracted with ethyl acetate. The organic layer was washed with 1% aqueous hydrochloric acid and with water then dried and evaporated. The residue was chromatographed over silica gel with 5% methanol in chloroform to give 36 mg orange solid, $R_f = 0.18$ with methanol:chloroform (1:4). Absorbance maxima in 40 mM potassium phosphate buffer at pH 9.0 at 480 and 508 nm; (extinction coefficients of 23,500 $cm^{-1} M^{-1}$ and 26,200 $cm^{-1} M^{-1}$, respectively).

EXAMPLE 5

Preparation of 3-acetoxy-5'-carboxy-10-dimethylamino-spiro[7H-benzo[c]xanthene-7,1'(3'H)-isobenzofuran]-3'-one, 14.

To prepare the acetate from 8, 300 mg 5'-carboxy-10-dimethylamino-3-hydroxy-spiro[7H-benzo[c]xanthene-7,1'(3'H)-isobenzofuran]-3'-one was added 5 ml acetic anhydride and the solution refluxed for 2 hours. The solution was poured into water and stirred overnight to hydrolyze excess actic anhydride. The resulting solid was collected and purified by silica gel chromatography with 10% methanol with chloroform to give 0.16 g dark violet solid, $R_f = 0.37$ with methanol:chloroform (1:9). Absorbance maxima in potassium phosphate buffer at pH 7.0 at 511 and 540 nm; extinction coefficients of 24,100 and 21,700 $cm^{-1} M^{-1}$ respectively.

EXAMPLE 6

Preparation of 3-acetoxy-5'-acetoxymethoxycarbonyl-10-dimethylamino-spiro[7H-benzo[c]xanthene-7,1'(3'H)-isobenzofuran]-3'-one, 15.

To form the acetoxymethyl ester of 8, 100 mg 5'-carboxy-10-dimethylamino-3-hydroxy-spiro[7H-benzo[c]xanthene-7,1'(3'H)-isobenzofuran]-3'-one was stirred in 5 ml chloroform containing 90 mg diisopropylethylamine and 160 mg bromomethyl acetate. The mixture was stirred overnight and chromatographed over silica gel with chloroform to yield 51 mg of an orange oil, $R_f = 0.46$ with methanol:chloroform (1:40). The $^1H$ NMR spectrum showed the presence of both an aromatic and an aliphatic acetate resonance (3H each) and a single methylene signal (2H). Mass spectrum M+1 peak = 568 atomic mass units.

EXAMPLE 7

Methods for determination of the $pK_a$ for the benzo[c]xanthene indicators.

A stock solution was prepared by dissolving 7.6 mg of compound 3 in 2.00 ml methanol. The stock solution was diluted ten-fold into 40 mM pH 9.00 potassium phosphate buffer. Absorbance solutions were prepared by further diluting 25 μl of the aqueous stock solution to 2.025 ml with 40 mM potassium phosphate buffers of the appropriate pH. Absorbance ratios at 480 nm versus 494 nm and 537 nm versus 494 nm were obtained for the solutions at pH 4.10, 4.60, 5.20, 5.60, 5.95, 6.60, 6.90, 7.40, 7.60, 7.80, 7.90, 8.25, 8.59, 8.90, 9.00, 10.10, 10.60, 11.10, and 11.70 on an IBM Model 9420 UV/Visible Spectrophotometer. $pK_a$'s were obtained from a plot of the absorbance ratios versus pH as in FIG. 4b and are tabulated in Table 2.

TABLE 2

| SPECTRAL CHARACTERISTICS OF BENZO[C]XANTHENE INDICATORS DYES | | | | | | | | |
|---|---|---|---|---|---|---|---|---|
| ABSORPTION (NM) (EXTINCTION COEFFIECIENT $10^3 cm^{-1} M^{-1}$) | | | | | | FLUORESCENCE (NM) | | |
| # | ACID MAXIMA | | BASE MAXIMUM | $pK_a$ | ACID EXCITE | ACID EMIT | BASE EXCITE | BASE EMIT | APPROX. QY. |
| 1 | 480 (24.8) | 508 (28.2) | 537 (49.7) | 7.85 | 513 | 539 | 540 | 618 | 0.34 |
| 2 | 479 (22.8) | 508 (28.5) | 537 (44.4) | 7.80 | 514 | 543 | 543 | 623 | 0.35 |
| 3 | 485 (20.5) | 514 (25.3) | 547 (40.4) | 7.65 | 517 | 546 | 552 | 630 | 0.48 |
| 4 | 477 (19.8) | 507 (21.8) | 537 (33.7) | 8.00 | 513 | 541 | 537 | 626 | 0.35 |
| 5 | 515 | 544 | 573 | 7.60 | 549 | 585 | 582 | 632 | 0.19 |

TABLE 2-continued
SPECTRAL CHARACTERISTICS OF BENZO[C]XANTHENE INDICATORS DYES

| # | ABSORPTION (NM) (EXTINCTION COEFFIECIENT $10^3$ cm$^{-1}$ M$^{-1}$) | | | $pK_a$ | ACID EXCITE | ACID EMIT | FLUORESCENCE (NM) | | APPROX. QY. |
|---|---|---|---|---|---|---|---|---|---|
|   | ACID MAXIMA | BASE MAXIMUM | | | | | BASE EXCITE | BASE EMIT | |
|   | (17.7) | (21.6) | (44.1) | | | | | | |
| 6 | 518 | 550 | 577 | 7.50 | 557 | 583 | 582 | 632 | 0.23 |
|   | (20.5) | (24.4) | (46.4) | | | | | | |
| 7 | 495 | 522 | 552 | 7.70 | 525 | 552 | 558 | 629 | 0.38 |
| 8 | 518 | 548 | 574 | 7.50 | 556 | 587 | 581 | 636 | 0.20 |
|   | (23.2) | (25.7) | (44.9) | | | | | | |
| 9 | 517 | 550 | 577 | 7.75 | 558 | 583 | 582 | 633 | 0.24 |
|   | (26.2) | (29.7) | (51.5) | | | | | | |
| 10 | 496 | 524 | 556 | 7.75 | 526 | 555 | 557 | 635 | 0.43 |
| 11 | 529 | 569 | 587 | 7.90 | 530 | 599 | 590 | 630 | 0.35 |
|   | (22.2) | (19.4) | (38.7) | | | | | | |

Fluorescence data was obtained on a Perkin-Elmer Model 650-40 Fluorescence Spectrophotometer with a Perkin-Elmer/Hitachi 057 X-Y Recorder using a tenfold dilution of the absorbance solutions. An estimate of the quantum yield of the dyes relative to fluorescein or sulforhodamine 101 was obtained by integrating the emission spectrum of the dye excited at the same optical density as the standard. These are tabulated in Table 2.

Figure 1B:
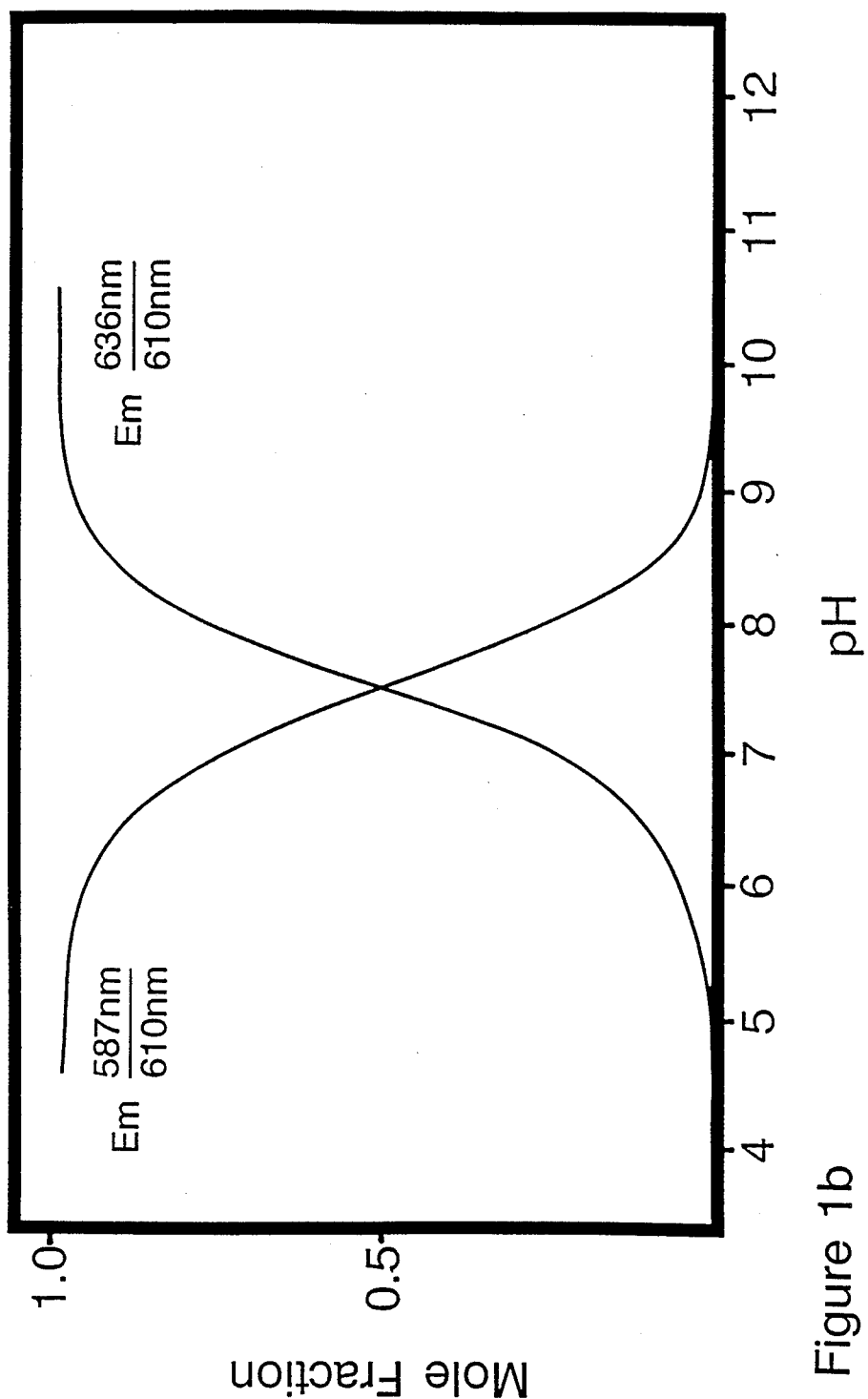

EXAMPLE 8
Examples of the practicality of the four methods described in the Summary of the Invention Method 1, observation of dual emission with a single excitation, is shown in FIG. 1 for compound 8. Solutions of the dye in buffers of defined pH were excited at 514 nm and emission recorded (FIG. 1a). The ratio of the emission intensity at 636 nm versus 610 nm and of emission at 587 nm versus 610 nm were determined as a function of pH (FIG. 1b).

Figure 2A:
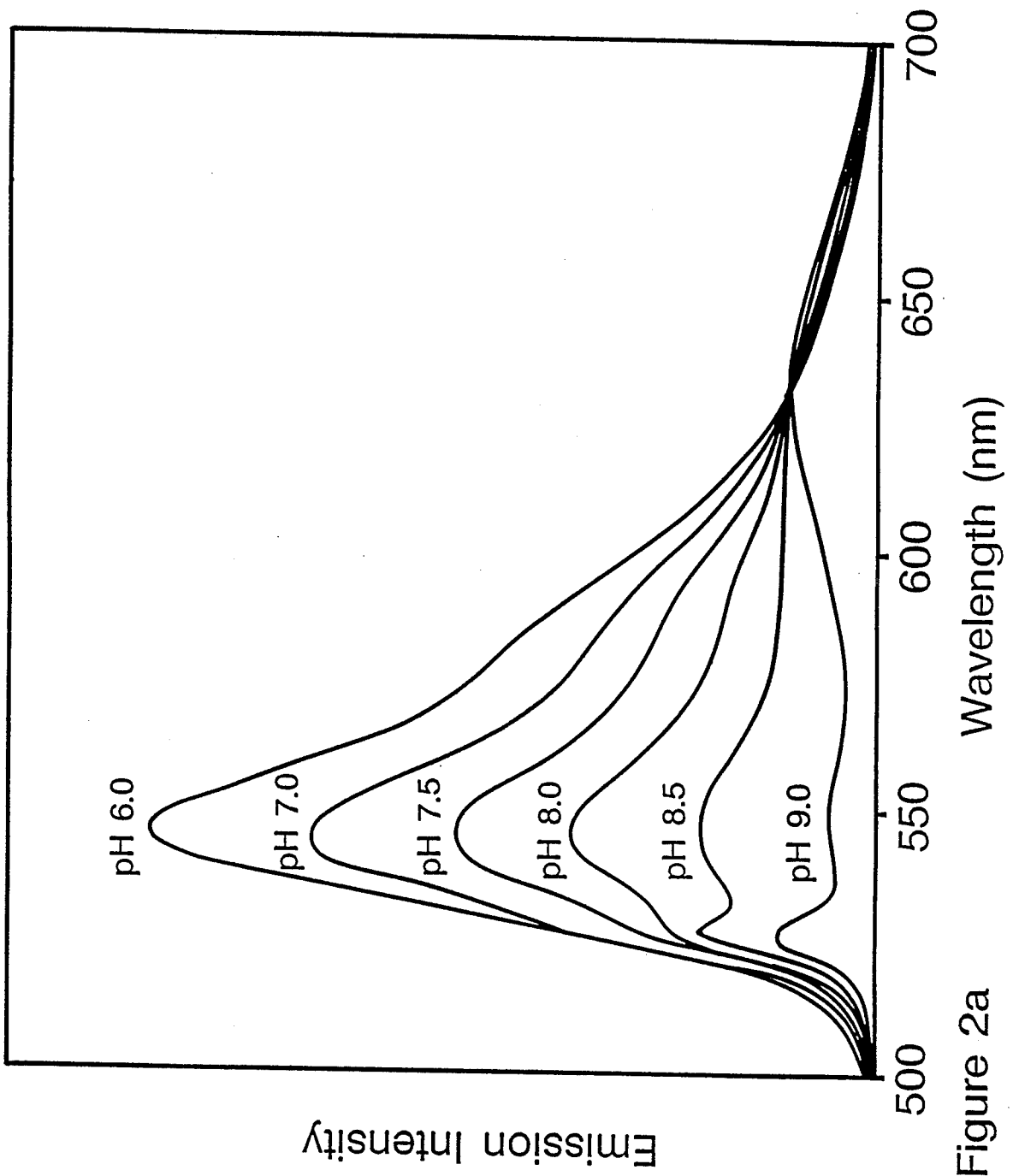
FIGS. 2a and 2b: use of two excitation wavelengths and two emission wavelengths is demonstrated in FIG. 2 for compound 3. Solutions of the dye were excited at 525 nm where the acid form is the predominant absorbing species and at 568 nm where the base form is the predominant absorbing species.
Figure 2B:
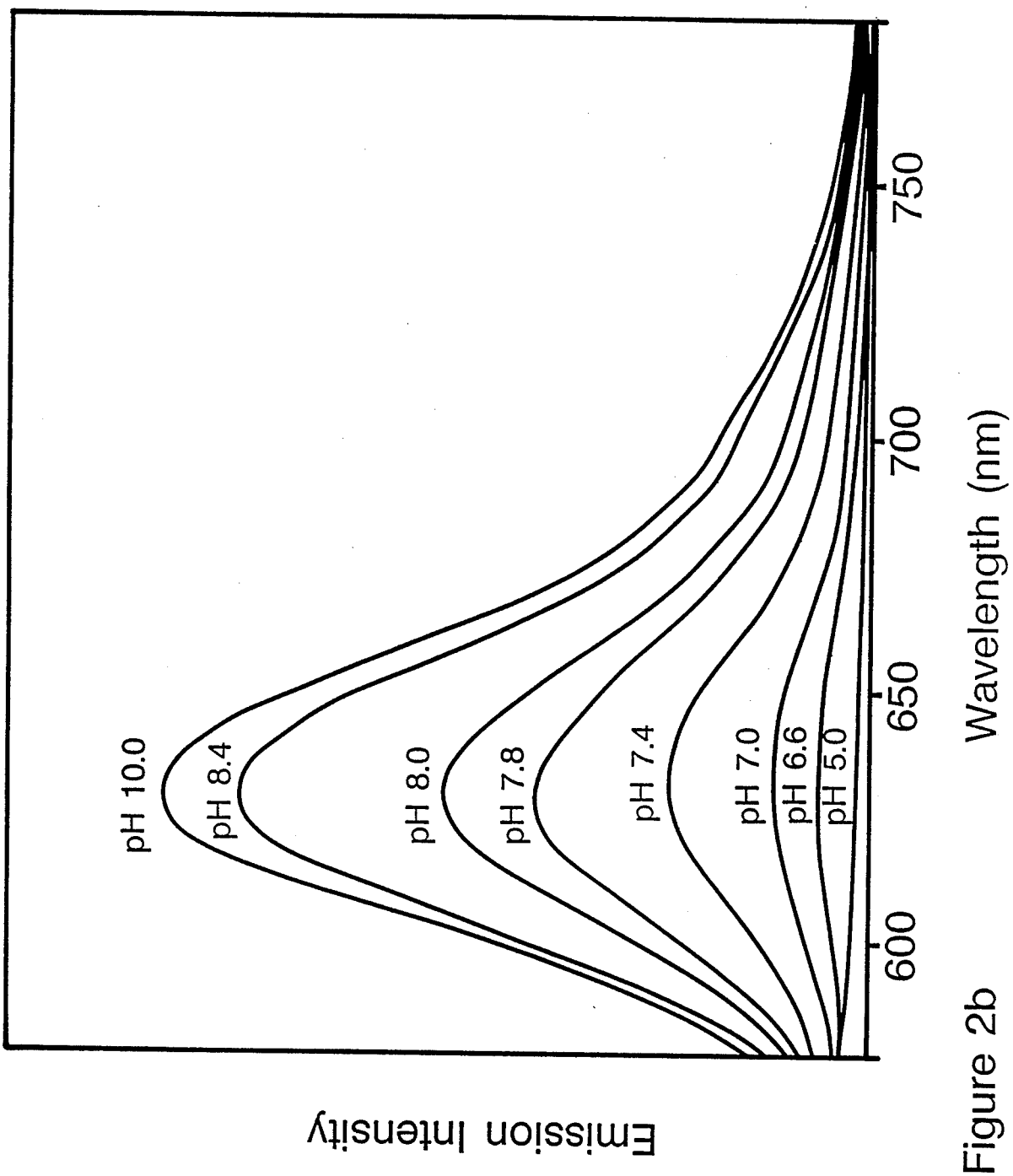

Method 2, use of two excitation wavelengths and two emission wavelengths, is demonstrated in FIG. 2 for compound 3. Solutions of the dye were excited at 525 nm where the acid form is the predominant absorbing species and at 568 nm where the base form is the predominant absorbing species.

Figure 3A:
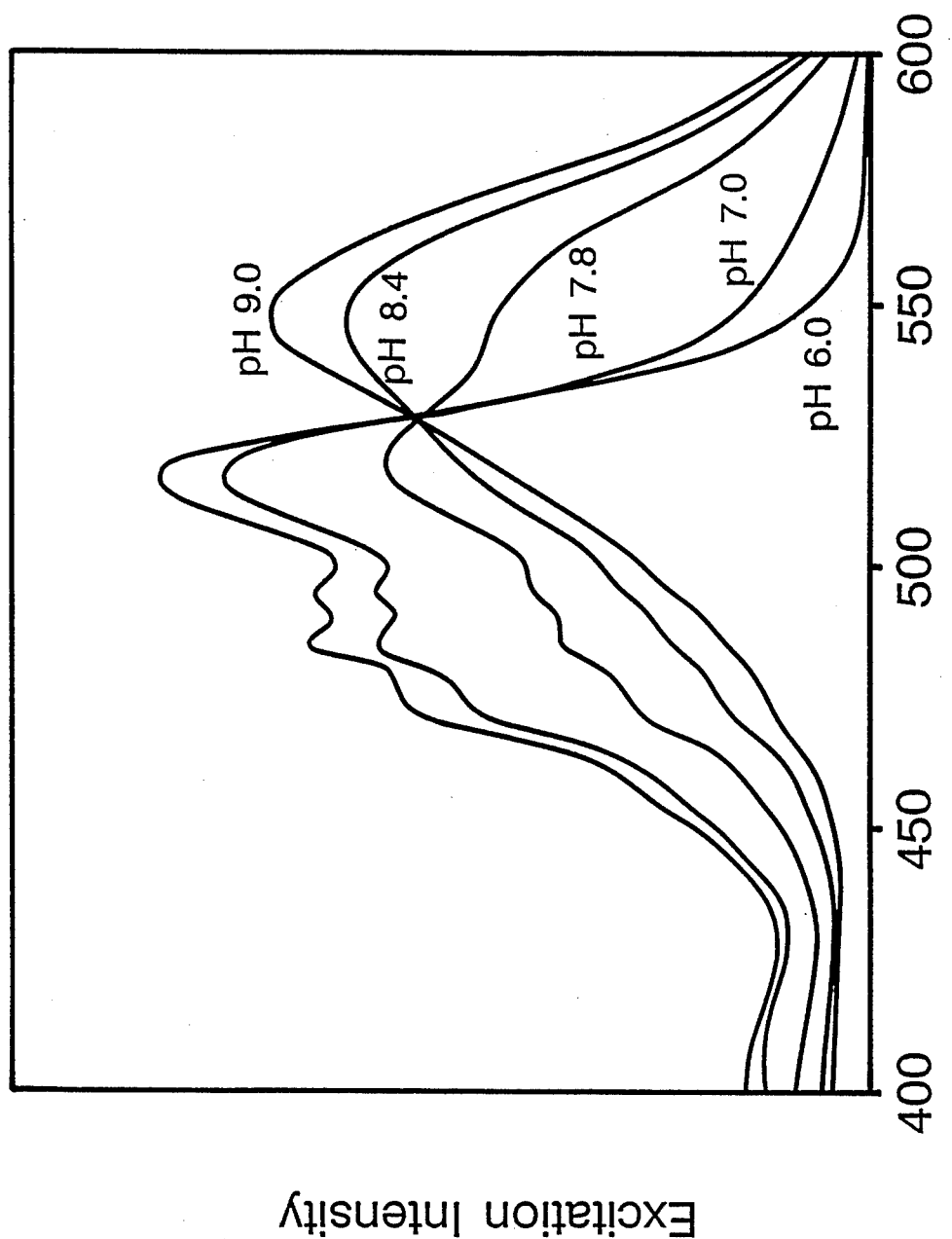
FIGS. 3a and 3b: using one emission wavelength and two excitation wavelengths is illustrated in FIG. 3 for compound 3. Excitation spectra were determined for the dye while observing the emission at 620 nm as in FIG. 3a. The ratios of excitation intensity at 476 nm versus 530 nm and at 552 nm versus 530 nm as a function of pH are shown in FIG. 3b.
Figure 3B:
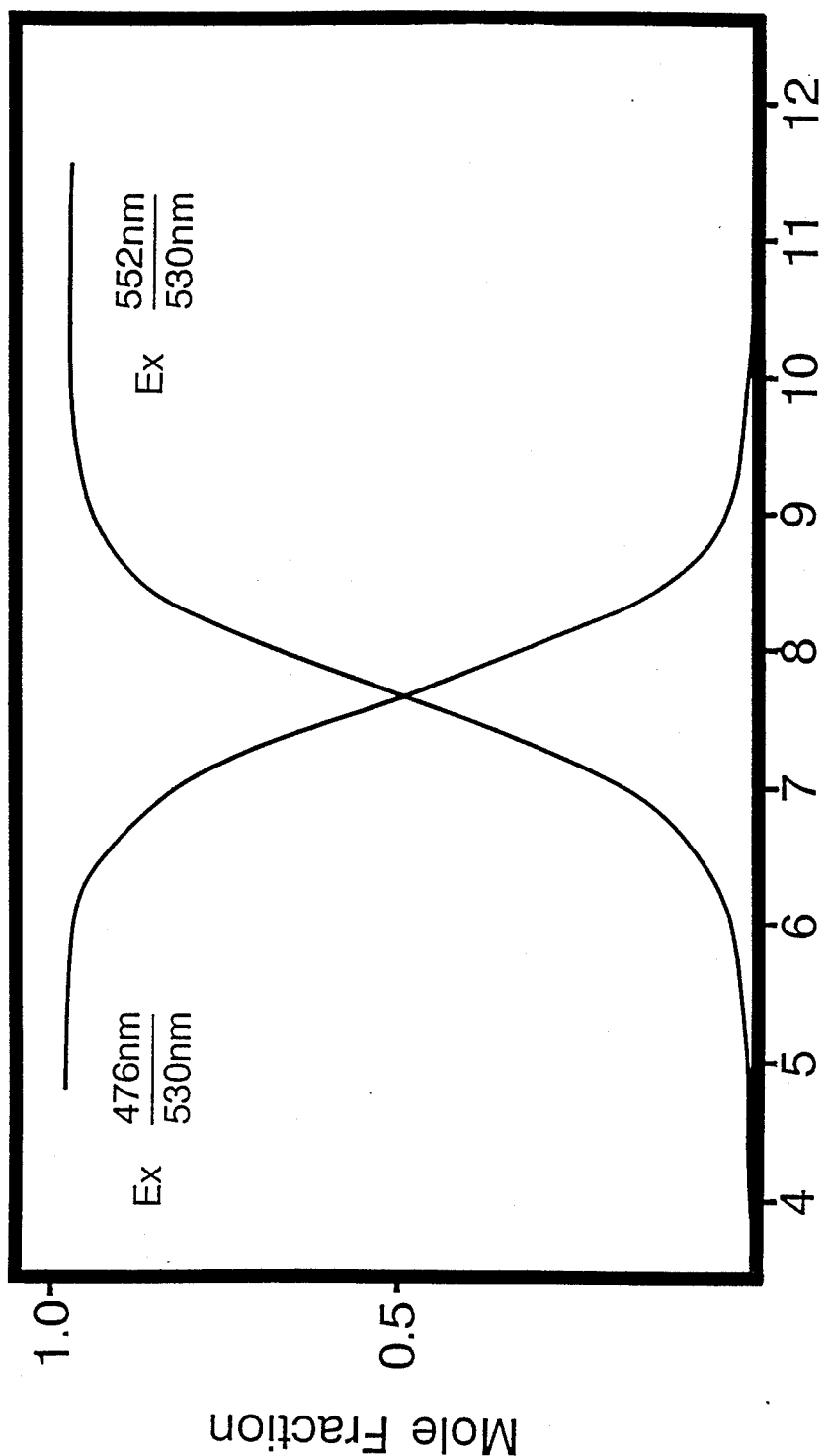

Method 3, using one emission wavelength and two excitation wavelengths, is illustrated in FIG. 3 for compound 3. Excitation spectra were determined for the dye while observing the emission at 620 nm as in FIG. 3a. The ratios of excitation intensity at 476 nm versus 530 nm and at 552 nm versus 530 nm as a function of pH are shown in FIG. 3b.

Figure 4A:
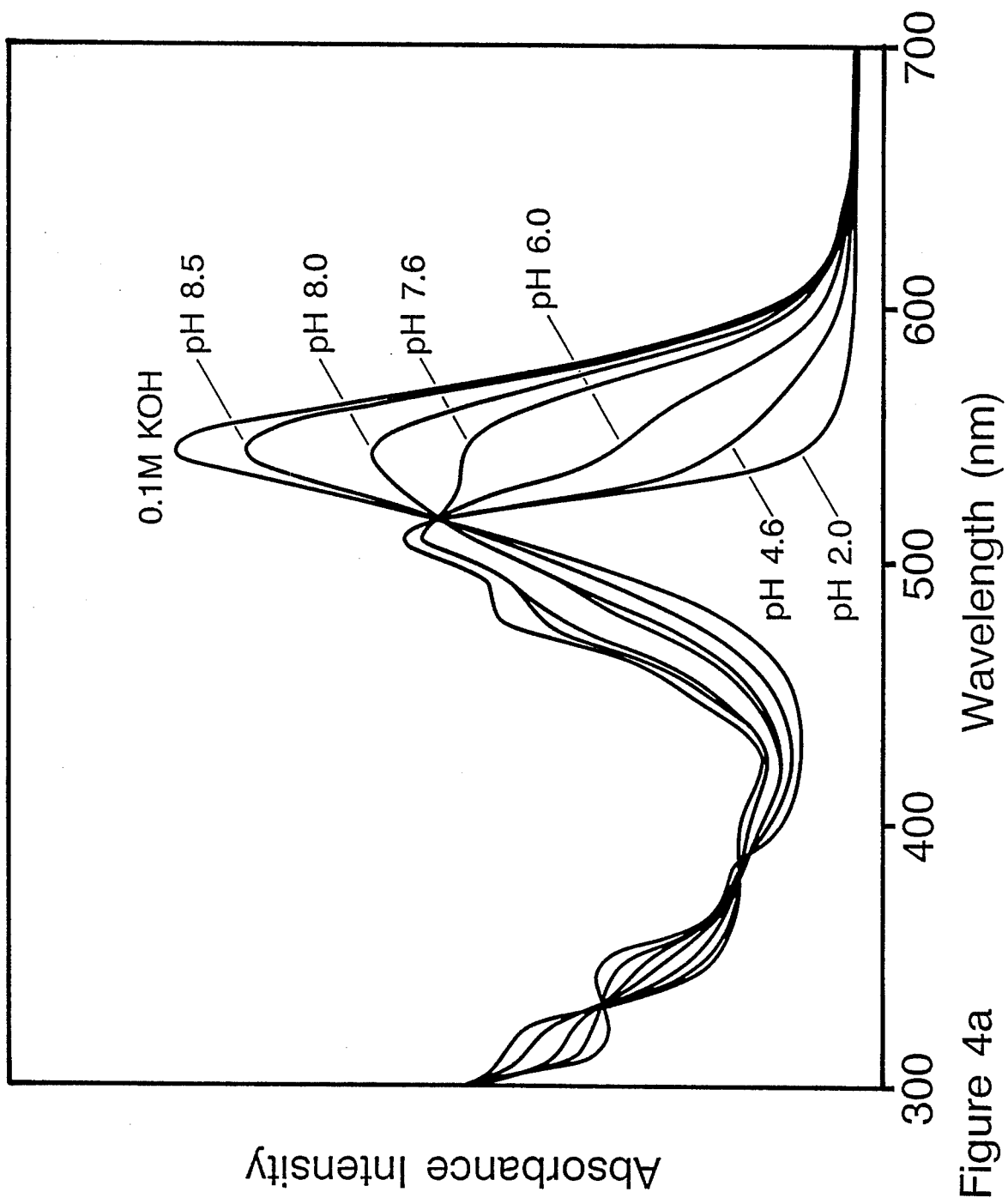
FIGS. 4a and 4b: measurement of pH dependent absorption spectra is demonstrated in FIG. 4 for compound 3. Absorption spectra of the dye in solutions of various pH were recorded (FIG. 4a) and the ratio of absorbance at 545 nm versus 519 nm or 485 nm versus 519 nm was determined at each pH. The pH dependence of this ratio is shown in FIG. 4b.
Figure 4B:
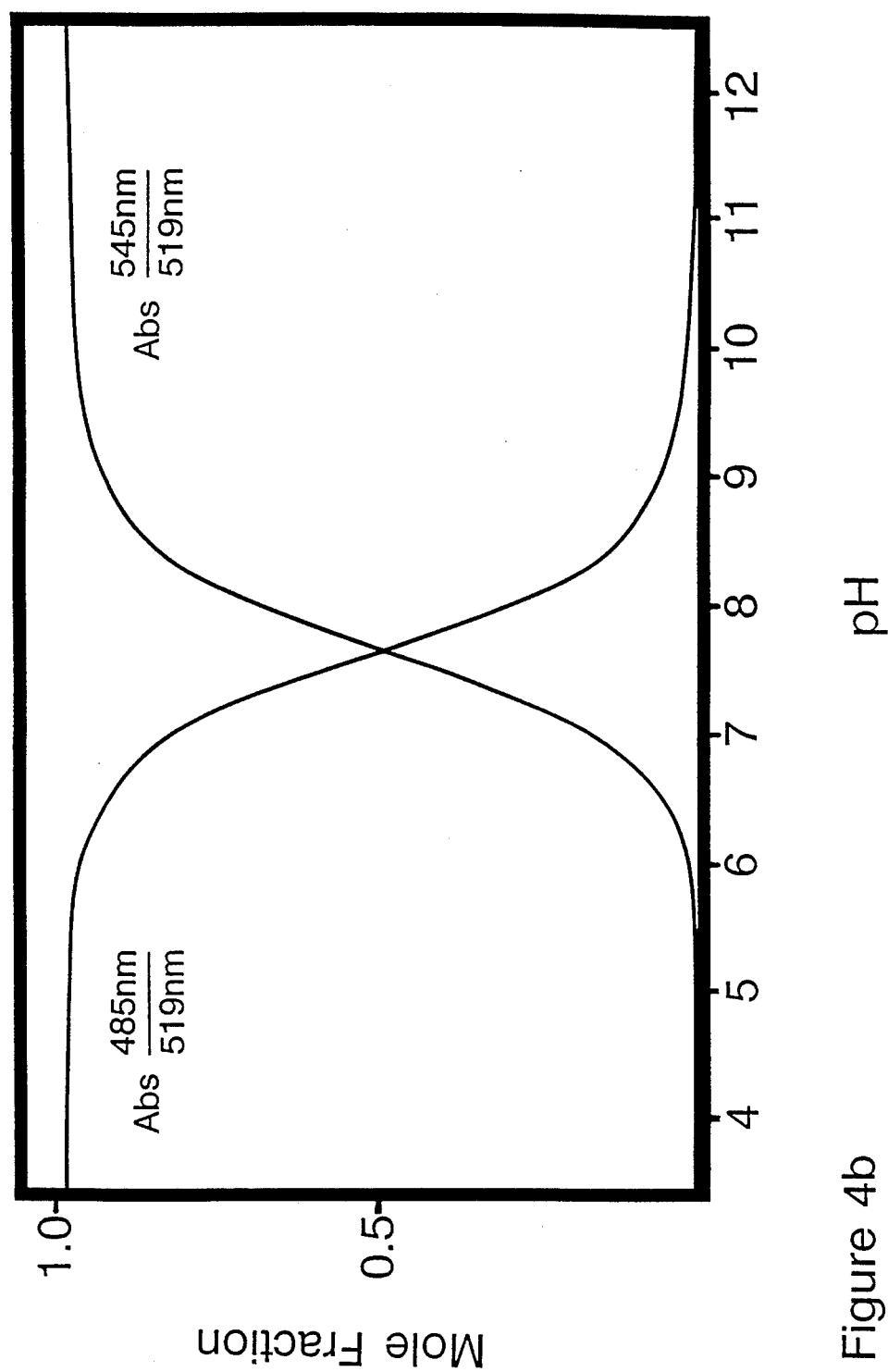

Method 4, measurement of pH dependent absorption spectra, is demonstrated in FIG. 4 for compound 3. Absorption spectra of the dye in solutions of various pH were recorded (FIG. 4a) and the ratio of absorbance at 545 nm versus 519 nm or 485 nm versus 519 nm was determined at each pH. The pH dependence of this ratio is shown in FIG. 4b.

For purposes of the invention and its claims it is recognized that the term "wavelength" includes all wavelengths that are passed by the monochrometer, filter, or other light selection device.

Although the foregoing invention has been described in some detail by way of illustration and example for purposes of clarity and understanding, it will be obvious that certain changes and modifications may be practiced within the scope of the appended claims.

We claim:
1. A compound of the formula:

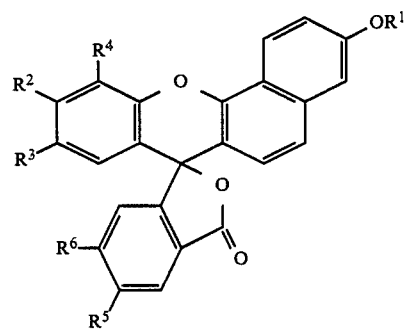

wherein:
$R^1$ is hydrogen, acetyl or methyl,
$R^2$ is hydroxyl, acetoxyl, dimethylamino, diethylamino, ethylamino or methoxyl
$R^3$ is hydrogen, hydroxyl, halo, methyl or carboxyethyl
$R^4$ is hydrogen,
$R^5$ is hydrogen, carboxyl or acetoxymethoxycarbonyl, and
$R^6$ is hydrogen, carboxyl or acetoxymethoxycarbonyl.

2. The compound of claim 1 wherein $R^1$, $R^3$, $R^4$, $R^5$ and $R^6$ are hydrogen, and $R^2$ is hydroxy.

3. The compound of claim 1 wherein $R^3$, $R^4$, $R^5$ and $R^6$ are hydrogen, $R^1$ is acetyl and $R^2$ is acetoxy.

4. The compound of claim 1 wherein $R^1$, $R^3$, $R^4$ and $R^5$ are hydrogen, $R^2$ is hydroxy and $R^6$ is carboxy.

5. The compound of claim 1 wherein $R^1$, $R^3$, $R^4$ and $R^6$ are hydrogen, $R^2$ is hydroxy and $R^5$ is carboxy.

6. The compound of claim 1 wherein $R^3$, $R^4$ and $R^5$ are hydrogen, $R^1$ is acetyl, $R^2$ is acetoxy and $R^6$ is carboxy.

7. The compound of claim 1 wherein $R^3$, $R^4$ and $R^6$ are hydrogen, $R^1$ is acetyl, $R^2$ is acetoxy and $R^5$ is carboxy.

8. The compound of claim 1 wherein $R^1$, $R^4$ and $R^5$ are hydrogen, $R^2$ is hydroxy, $R^3$ is chloro and $R^6$ is carboxy.

9. The compound of claim 1 wherein $R^1$, $R^4$ and $R^6$ are hydrogen, $R^2$ is hydroxy, $R^3$ is chloro and $R^5$ is carboxy.

10. The compound of claim 1 wherein $R^4$ and $R^5$ are hydrogen, $R^1$ is acetyl, $R^2$ is acetoxy, $R^3$ is chloro and $R^6$ is carboxy.

11. The compound of claim 1 wherein $R^4$ and $R^6$ are hydrogen, $R^1$ is acetyl, $R^2$ is acetoxy, $R^3$ is chloro and $R^5$ is carboxy.

12. The compound of claim 1 wherein $R^1$, $R^3$, $R^4$ and $R^5$ are hydrogen, $R^2$ is N,N-dimethylamino and $R^6$ is carboxy.

13. The compound of claim 1 wherein $R^1$, $R^3$, $R^4$ and $R^6$ are hydrogen, $R^2$ is N,N-dimethylamino and $R^5$ is carboxy.

14. The compound of claim 1 wherein $R^3$, $R^4$ and $R^5$ are hydrogen, $R^1$ is acetyl, $R^2$ is N,N-dimethylamino and $R^6$ is acetoxymethoxycarbonyl.

15. The compound of claim 1 wherein $R^3$, $R^4$ and $R^6$ are hydrogen, $R^1$ is acetyl, $R^2$ is N,N-dimethylamino and $R^5$ is acetoxymethoxycarbonyl.

16. The compound of claim 1 wherein $R^1$, $R^3$, $R^4$ and $R^5$ are hydrogen, $R^2$ is N,N-diethylamino and $R^6$ is carboxy.

17. The compound of claim 1 wherein $R^1$, $R^3$, $R^4$ and $R^6$ are hydrogen, $R^2$ is N,N-diethylamino and $R^5$ is carboxy.

18. The compound of claim 1 wherein $R^3$, $R^4$ and $R^5$ are hydrogen, $R^1$ is acetyl, $R^2$ is N,N-diethylamino and $R^6$ is acetoxymethoxycarbonyl.

19. The compound of claim 1 wherein $R^3$, $R^4$ and $R^6$ are hydrogen, $R^1$ is acetyl, $R^2$ is N,N-diethylamino and $R^5$ is acetoxymethoxycarbonyl.

20. The compound of claim 1 wherein $R^1$, $R^4$ and $R^5$ are hydrogen, $R^2$ is N-ethylamino, $R^3$ is methyl and $R^6$ is carboxy.

21. The compound of claim 1 wherein $R^1$, $R^4$ and $R^6$ are hydrogen, $R^2$ is N-ethylamino, $R^3$ is methyl and $R^5$ is carboxy.

22. A compound of the formula:

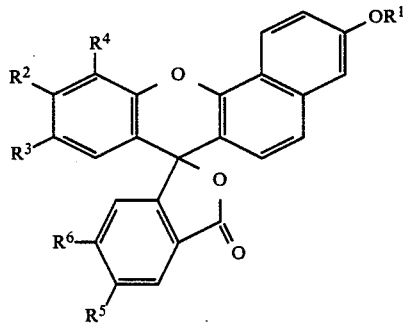

wherein:
$R^1$ is hydrogen, acetyl or methyl,
$R^2$ is N,N-dialkylamine, of which each alkyl group consists of 3 methylene groups which, in conjunction with $R^3$ and $R^4$, complete two six-membered non-aromatic rings chemically bonded to the aromatic ring of benzo[c]xanthene, and
$R^5$ and $R^6$, which may be the same or different, are hydrogen, carboxyl or acetoxymethoxycarbonyl.

23. The compound of claim 22 wherein:
$R^1$ and $R^5$ are hydrogen; and
$R^6$ is carboxyl.

24. The compound of claim 22 wherein:
$R^1$ and $R^6$ are hydrogen; and
$R^5$ is carboxyl.

25. A compound of the formula:

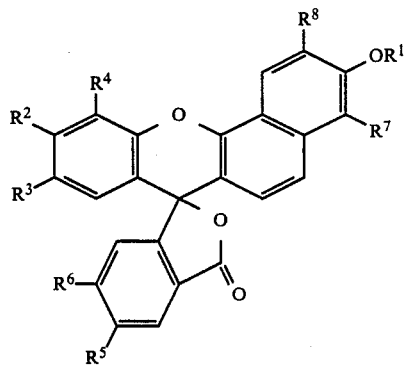

wherein:
$R^1$ is hydrogen, a metal or non-metal salt, an alkyl or aryl ether containing from 1 to 18 carbon atoms, or an ester of an aliphatic acid containing from 1 to 18 carbon atoms;
$R^2$ is hydroxyl, amino, or an amino modified by formation of an alkylether, alkylester, alkylamide or alkylamine derivative containing 1 to 18 carbon atoms;
$R^5$ and $R^6$, which may be the same or different, are carboxy, sulfo, or alkylamido containing 1 to 6 carbon atoms; and
$R^3$, $R^4$, $R^7$ and $R^8$, which may be the same or different, are alkoxyl containing from 1 to 6 carbon atoms, alkyl containing from 1 to 6 carbon atoms, haloalkyl containing from 1 to 6 carbon atoms, or halo.

* * * * *

UNITED STATES PATENT AND TRADEMARK OFFICE
CERTIFICATE OF CORRECTION

PATENT NO. : 4,945,171

DATED : 07/31/90

INVENTOR(S) : R.P. Haugland and J.E. Whitaker

It is certified that error appears in the above-identified patent and that said Letters Patent is hereby corrected as shown below:

Column 1, above "BACKGROUND OF THE INVENTION", insert --This invention was made with government support under grant number 37347 awarded by the National Institutes of Health. The government has certain rights in this invention.

Signed and Sealed this

First Day of March, 1994

Attest:

BRUCE LEHMAN

*Attesting Officer*  *Commissioner of Patents and Trademarks*